United States Patent
Suzuki

(10) Patent No.: US 8,123,746 B2
(45) Date of Patent: Feb. 28, 2012

(54) HIGH-FREQUENCY CURRENT TREATMENT TOOL

(75) Inventor: Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 474 days.

(21) Appl. No.: 11/510,305

(22) Filed: Aug. 25, 2006

(65) Prior Publication Data

US 2007/0203489 A1 Aug. 30, 2007

Related U.S. Application Data

(63) Continuation-in-part of application No. 10/830,799, filed on Apr. 23, 2004, now abandoned, which is a continuation-in-part of application No. 10/855,071, filed on May 27, 2004, now abandoned.

(30) Foreign Application Priority Data

Apr. 28, 2003 (JP) ................................ 2003-123527
May 29, 2003 (JP) ................................ 2003-152605

(51) Int. Cl.
*A61B 18/14* (2006.01)
(52) U.S. Cl. ................. 606/51; 606/52; 606/48; 606/45
(58) Field of Classification Search .............. 606/50–52, 606/205–207, 45, 48; 10/50–52
See application file for complete search history.

(56) References Cited

U.S. PATENT DOCUMENTS

| | | | |
|---|---|---|---|
| 5,431,674 A | 7/1995 | Basile et al. | |
| 5,443,463 A * | 8/1995 | Stern et al. | 606/51 |
| 5,746,740 A | 5/1998 | Nicholas | |
| 5,827,281 A | 10/1998 | Levin | |
| 5,876,401 A * | 3/1999 | Schulze et al. | 606/51 |
| 5,891,142 A | 4/1999 | Eggers et al. | |
| 6,039,735 A | 3/2000 | Greep | |
| 6,113,598 A * | 9/2000 | Baker | 606/51 |
| 6,273,887 B1 | 8/2001 | Yamauchi et al. | |
| 6,494,881 B1 | 12/2002 | Bales et al. | |
| 6,860,880 B2 | 3/2005 | Treat et al. | |
| 2002/0091383 A1 | 7/2002 | Hooven | |
| 2003/0009164 A1 | 1/2003 | Woloszko | |
| 2003/0171747 A1* | 9/2003 | Kanehira et al. | 606/45 |
| 2004/0006340 A1 | 1/2004 | Latterell et al. | |
| 2005/0010211 A1 | 1/2005 | Suzuki | |

FOREIGN PATENT DOCUMENTS

| | | |
|---|---|---|
| JP | HEI 5-253241 | 10/1993 |
| JP | 8-299355 | 11/1996 |
| JP | HEI 08-29355 | 11/1996 |
| JP | 9-94214 | 4/1997 |
| JP | 2000-139943 | 5/2000 |

(Continued)

*Primary Examiner* — Linda Dvorak
*Assistant Examiner* — Amanda Scott
(74) *Attorney, Agent, or Firm* — Scully, Scott, Murphy & Presser, P.C.

(57) ABSTRACT

A high-frequency current treatment tool of the present invention includes a pair of clamp pieces which clamps an object, and an electrode which is provided on one of the clamp pieces. Each of the clamp pieces has a clamp face which faces with each other. A first clamp face being one of the clamp faces has a chevron shape protruding toward a second clamp face being another of the clamp faces, and having a ridge portion formed along a longitudinal direction of the first clamp face. The electrode is arranged along the ridge portion.

6 Claims, 14 Drawing Sheets

FOREIGN PATENT DOCUMENTS

| | | |
|---|---|---|
| JP | 2001-517529 | 10/2001 |
| JP | 2001-518344 | 10/2001 |
| JP | 2001-340349 | 12/2001 |
| JP | 2004-321660 | 11/2004 |
| WO | WO 01/15614 | 3/2001 |
| WO | WO 01/28444 | 4/2001 |
| WO | WO 02/087454 A1 | 11/2002 |
| WO | WO 03/005882 A2 | 1/2003 |

* cited by examiner

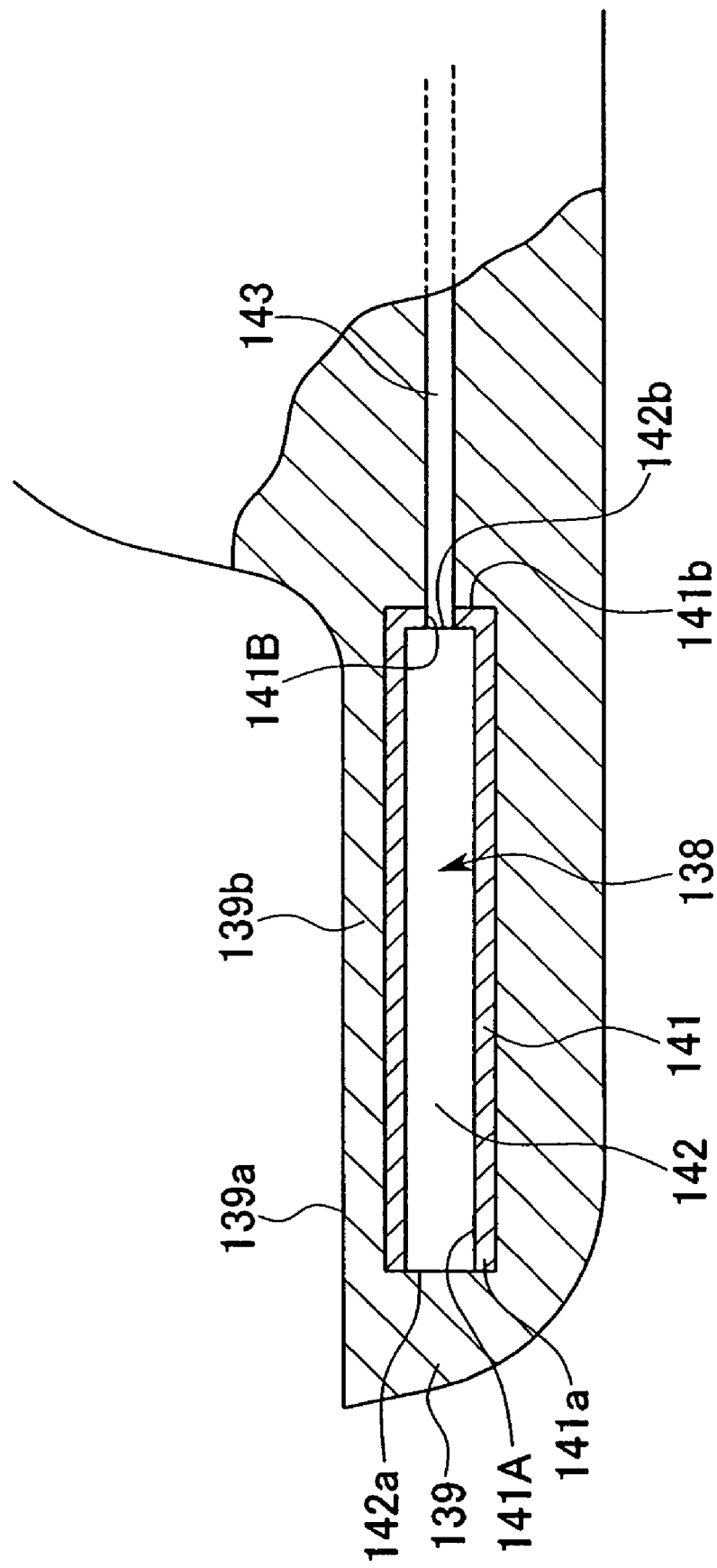

HIGH-FREQUENCY CURRENT TREATMENT TOOL

This application is a Continuation In-Part Application of: U.S. patent application Ser. No. 10/830,799, filed Apr. 23, 2004 now abandoned, which claims priority on Japanese Patent Application No. 2003-123527, filed Apr. 28, 2003; and U.S. patent application Ser. No. 10/855,071, filed May 27, 2004 now abandoned, which claims priority on Japanese Patent Application No. 2003-152605, filed May 29, 2003, the contents of which are incorporated herein by reference.

BACKGROUND OF THE INVENTION

1. Field of the Invention

The present invention relates to a high-frequency current treatment tool which is to be used in treatments such as incision of a tissue by inserting it into a living organ and by supplying high-frequency current on the tissue.

2. Description of Related Art

High-frequency current treatment tools (an endoscopic forceps) are used for variety kinds of endoscopic procedures for excising a tissue. As one of such high-frequency current treatment tools, a high-frequency current forceps is known which excises a tissue by clamping the tissue with a tip portion thereof and supplying high-frequency current on the tissue.

As for the conventional high-frequency current forceps, several types are proposed such as: (i) a forceps having clamp faces which are formed on insulated clamp pieces so as to face with each other, and electrodes provided on each of the clamp faces (for example, refer to FIG. 2 of Japanese Unexamined Patent Application, First Publication No. H05-253241), (ii) a forceps having insulated scissors-type clamp pieces and electrodes provided on each clamp face of the clamp pieces which faces with each other (for example, refer to FIGS. 9 and 10 of U.S. Pat. No. 5,827,281), and (iii) a forceps having needle-shaped electrodes (for example, refer to FIG. 1 of Japanese Unexamined Patent Application, First Publication No. H08-299355).

Furthermore, as for a forceps which is not used together with an endoscope, one is also proposed which cauterizes or excises a living organ by exposing its wire-shaped electrodes (for example, refer to FIG. 5 of the specification of PCT International Publication No. WO01/28444).

SUMMARY OF THE INVENTION (1) A high-frequency current treatment tool of the present invention includes a pair of clamp pieces which clamps an object, and an electrode which is provided on one of the clamp pieces. Each of the clamp pieces has a clamp face which faces with each other. A first clamp face being one of the clamp faces has a chevron shape protruding toward a second clamp face being another of the clamp faces, and having a ridge portion formed along a longitudinal direction of the first clamp face. The electrode is arranged along the ridge portion.
(2) In the high-frequency current treatment tool according to the above (1), the electrode may be linear.
(3) In the high-frequency current treatment tool according to the above (2), a concave portion may be formed on the first clamp face at a middle position thereof in the longitudinal direction.
(4) In the high-frequency current treatment tool according to the above (3), the concave portion may be formed at a position between a distal end portion and a proximal end portion of the first clamp face along the ridge portion.
(5) In the high-frequency current treatment tool according to the above (4), the electrode may be installed at a position between a first ridge portion on the distal end portion and a second ridge portion on the proximal end portion.
(6) In the high-frequency current treatment tool according to the above (2), the electrode may be a wire.
(7) In the high-frequency current treatment tool according to the above (1), a corrugated portion may be formed on the second clamp face.
(8) In the high-frequency current treatment tool according to the above (1), the electrode may be provided inside a distal end of the first clamp face.
(9) In the high-frequency current treatment tool according to the above (1), a plurality of concave portions each of which crosses a longitudinal direction of the second clamp face may be formed on the second clamp face.
(10) Another high-frequency current treatment tool of the present invention includes a pair of clamp pieces which clamps an object, and a pair of electrodes each of which is provided on the clamp pieces. Each of the clamp pieces has a clamp face which faces with each other. Each of the clamp faces has a chevron shape protruding toward another clamp face and having a ridge portion formed along a longitudinal direction of the clamp face. Each of the electrodes is arranged along the ridge portions.
(11) In the high-frequency current treatment tool according to the above (10), the electrodes may be linear.
(12) In the high-frequency current treatment tool according to the above (11), each of the electrodes may be a wire.
(13) In the high-frequency current treatment tool according to the above (11), a concave portion may be formed on each of the clamp faces at middle positions thereof in the longitudinal direction.
(14) In the high-frequency current treatment tool according to the above (13), each of the concave portions may be formed at a position between a distal end portion and a proximal end portion of the clamp faces along the ridge portion.
(15) In the high-frequency current treatment tool according to the above (14), each of the electrodes may be installed at a position between a first ridge portion on the distal end portion and a second ridge portion on the proximal end portion.
(16) In the high-frequency current treatment tool according to the above (10), each of the electrodes may be provided inside a distal end of the clamp face.

BRIEF DESCRIPTION OF THE DRAWINGS

FIG. 19 is a cross-sectional view of an essential portion of a clamp piece of a forceps according to another related technology of the present invention.

DETAILED DESCRIPTION OF THE INVENTION

First Embodiment

A first embodiment of a high-frequency current treatment tool according to the present invention will be explained below referring to FIGS. 1 to 3.

Figure 1:
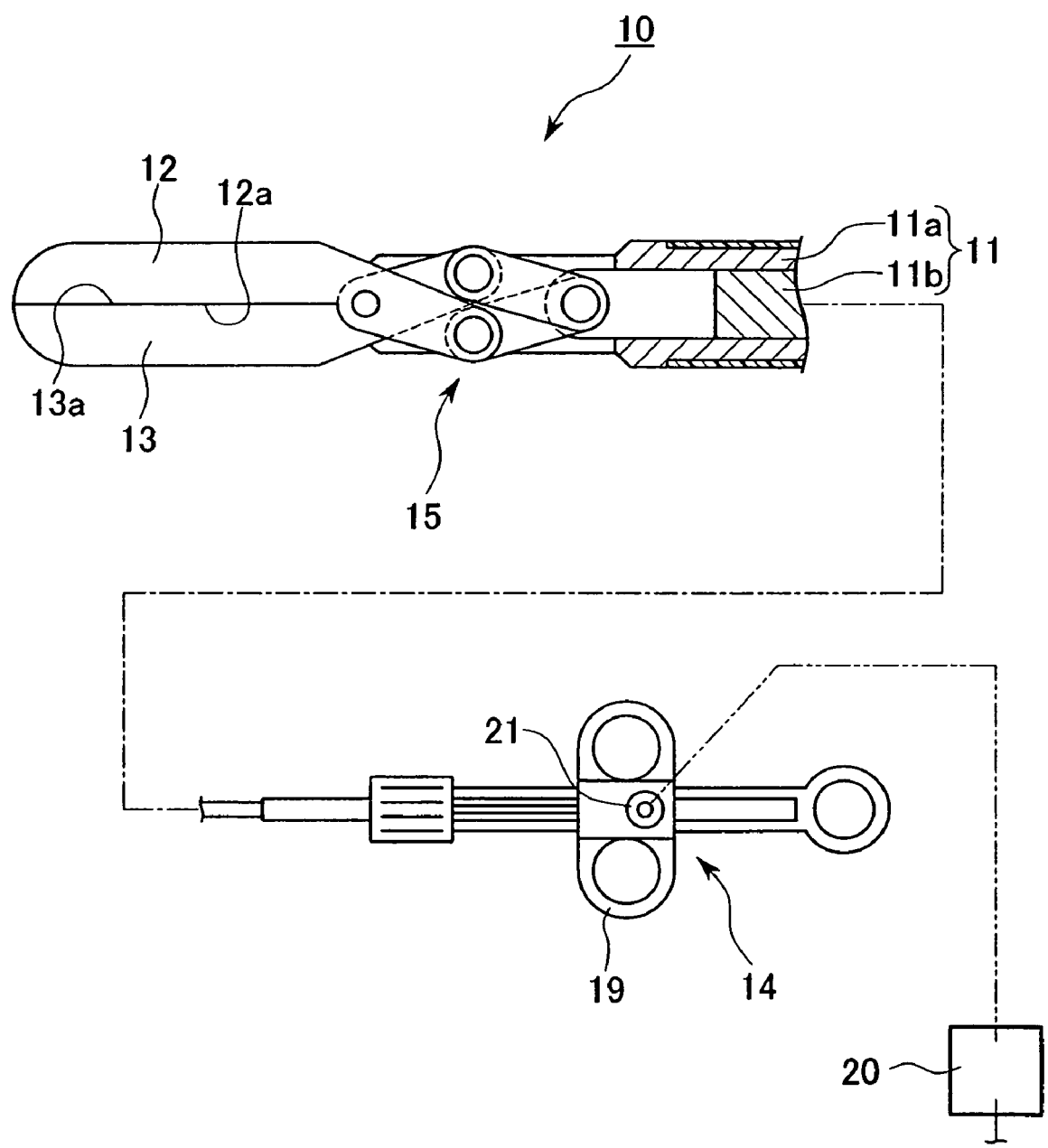
FIG. 1 is an explanatory view showing a high-frequency current forceps being a first embodiment of a high-frequency current treatment tool of the present invention.

As shown in FIG. 1, a high-frequency current forceps (the high-frequency current treatment tool) 10 according to the present embodiment has a flexible shaft member 11 to be inserted in a canal of an endoscope (not shown in the figures). A pair of clamp pieces 12 and 13 having a pair of clamp faces 12a and 13a facing with each other are provided at a distal end of the shaft member 11, while a controller 14 is provided at the bottom side of the shaft member 11.

The shaft member 11 has a flexible tube 11a and a control wire 11b inserted in the flexible tube 11a. A distal end of the control wire 11b is connected to the pair of clamp pieces 12 and 13 via a link mechanism 15. An outer periphery of the flexible tube 11a is covered with an electrical insulation cover.

Figure 2:
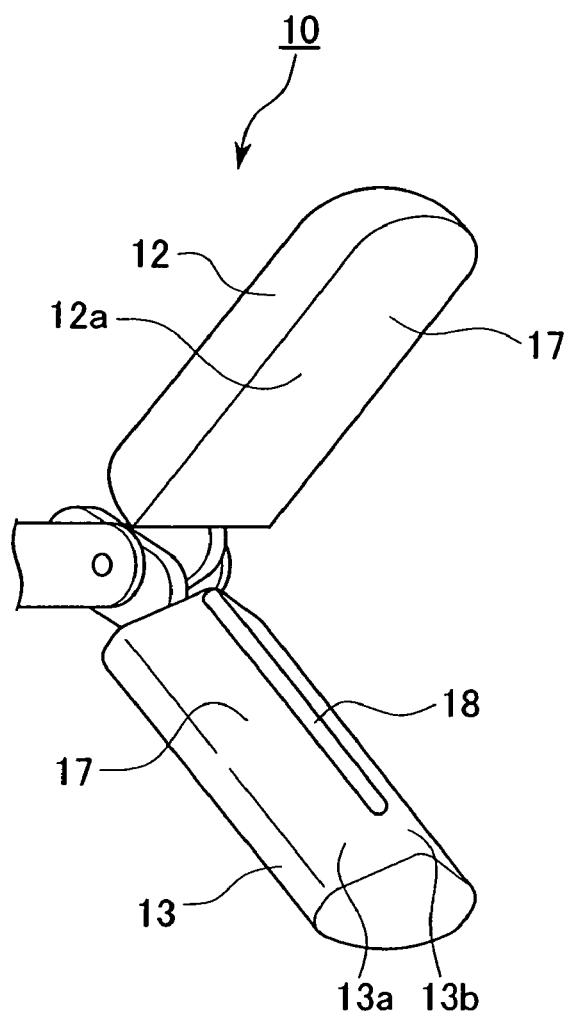
FIG. 2 is a perspective view of clamp pieces of the high-frequency current forceps.

The pair of clamp pieces 12 and 13 is made of metal such as stainless steel, and as shown in FIG. 2, the entire surface is electrically insulated by being covered with an insulation film 17.

The clamp face 12a is formed in planar shape, while the clamp face 13a is formed in a chevron shape and has a ridge portion 13b extending along a length direction of the clamp piece 13.

A linear electrode 18 which is not covered with the insulation film 17 is provided on the ridge portion 13b of the clamp face 13a. This electrode 18 is electrically connected to the control wire 11b via the clamp piece 13 and the link mechanism 15. Otherwise, one end of the electrode 18 may be electrically connected to the flexible tube 11a or the control wire 11b via a lead wire (not shown in the figures). Another end of the electrode 18 is provided within the clamp face 13a so that is does not protrude out from the outer shape of the clamp face 13a.

The controller 14 has a sliding controller 19 to which one end of the control wire 11b is connected, and a connection plug 21 for electrically connecting between the electrode 18 and one of the electrodes of a high-frequency power supply 20. Another electrode (not shown in the figures) of the high-frequency power supply 20 is connected to a skin of a human body so that a connection area therebetween is sufficiently larger than a connection area between a treatment part of the human body and the electrode 18.

Next, use of the high-frequency current forceps 10 according to the present embodiment having the above-mentioned construction will be explained referring to FIG. 3.

Firstly, an endoscope (not shown in the figures) is inserted into a body cavity of a human body. Then, an injection needle (not shown in the figures) is inserted into the body cavity through the endoscope, and a treatment part 22 which is to be excised is enlarged by injecting physiology salt solution into a lower layer of a mucous membrane of the treatment part 22. Thereafter, the high-frequency current forceps 10 is inserted into the body cavity through the endoscope. At this time, the sliding controller 19 maintains its backward position, and the pair of clamp pieces 12 and 13 keeps their closed state.

Next, the high-frequency current forceps 10 is operated. By moving the sliding controller 19 toward the forward position, the link mechanism 15 is driven via the control wire 11b, and then the pair of clamp pieces 12 and 13 is opened. Then, after applying the clamp faces 12a and 13a on the enlarged treatment part 22, the sliding controller 19 is again pulled backward. Then, the link mechanism 15 is driven in an opposite direction, and the pair of clamp pieces 12 and 13 closes.

In this condition, when high-frequency current is supplied to the electrode 18 by controlling the high-frequency power supply 20, high-frequency current is supplied through the human body to another electrode (not shown in the figures) pasted to the human body. At this time, current having very high electrical current density flows near around the electrode 18 because the electrode 18 is linear, and the surface area of the electrode 18 is sufficiently small. As a result, the living organ (i.e., the treatment part 22) contacting the electrode 18 is excised. Moreover, because the surfaces of the clamp pieces 12 and 13 except for the place where the electrode 18 is installed, are insulated, current density in a tissue except for the place where contacts the electrode 18 becomes very small.

After the incision, the treatment part 22 is removed by removing the endoscope out from the body cavity while maintaining the treatment part 22 clamped.

As has been explained in the above, the present embodiment adopts the high-frequency current forceps (the high-frequency current treatment tool) 10 including a pair of clamp pieces 12 and 13 which clamps the treatment part (an object) 22, and the electrode 18 which is provided on the clamp piece 13, wherein: each of the clamp pieces 12 and 13 has clamp faces 12a and 13a which faces with each other; the clamp face 13a (a first clamp face) being one of the clamp faces 12a and 13a has a chevron shape protruding toward the clamp face 12a (a second clamp face) being another of the clamp faces 12a and 13a and having the ridge portion 13b formed along a longitudinal direction of the clamp face 13a (first clamp face); and the electrode 18 is arranged along the ridge portion 13b. Furthermore, in the high-frequency current forceps 10, the electrode 18 is installed at a position between a first ridge portion on the distal end portion and a second ridge portion on the proximal end portion.

According to the above-mentioned high-frequency current forceps 10, because the linear electrode 18 is provided on the clamp face 13a, the surface area of the electrode 18 can easily be made smaller in relation to that of the conventional one; therefore, performance for incision can be improved by increasing the electrical current density.

Furthermore, because the electrode 18 is formed linearly and does not protrude out from the clamp face 13a, and because the exposed surface of the clamp piece 13 except for the location where the electrode 18 is installed is insulated, a part of the treatment part 22 to be contact with the electrode 18 can be limited within an area of an internal area of the clamp face 13a.

Second Embodiment

Figure 4:
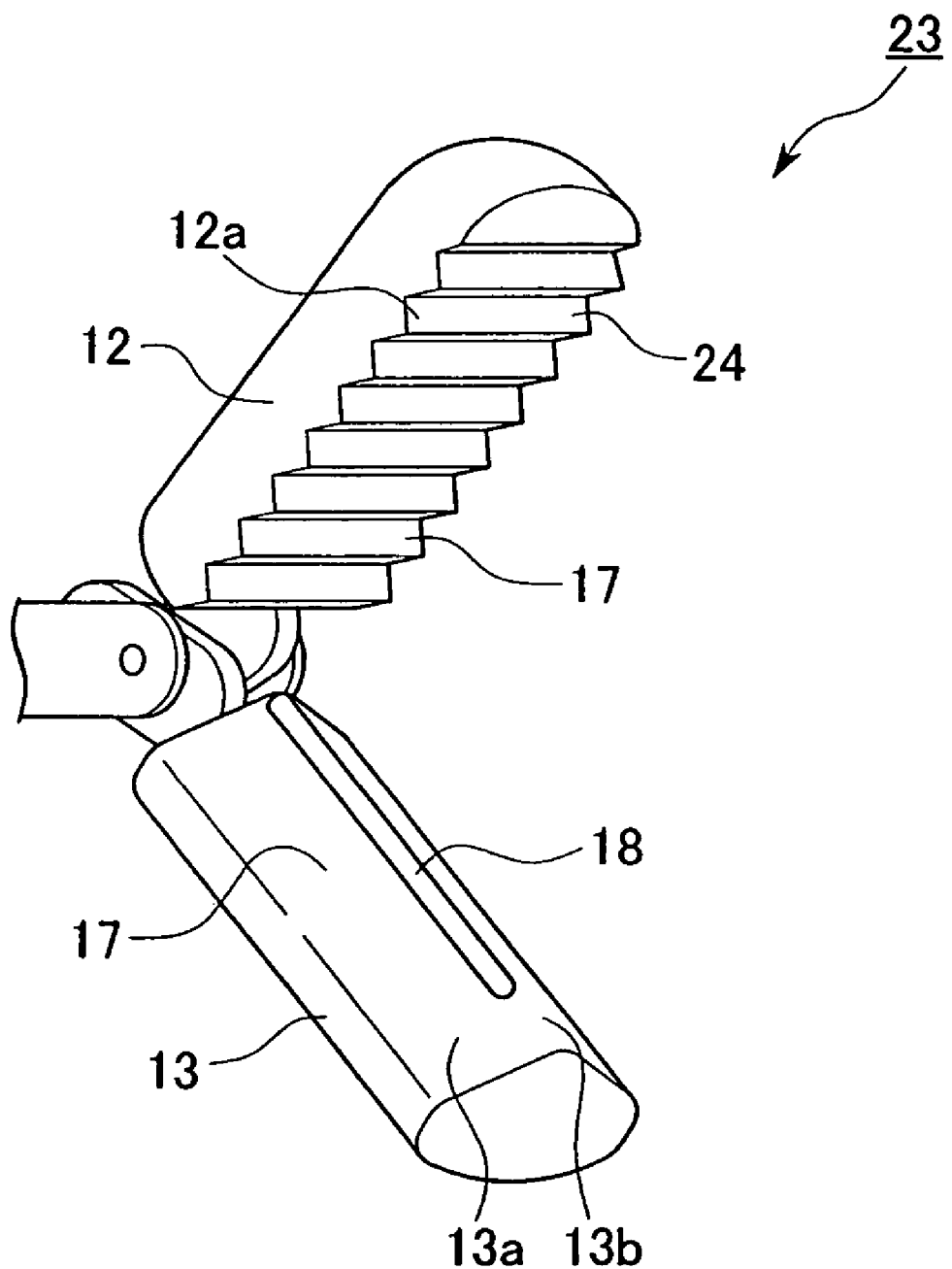
FIG. 4 is a perspective view of clamp pieces of a high-frequency current forceps being a second embodiment of a high-frequency current treatment tool of the present invention.

Next, a second embodiment of a high-frequency current treatment tool according to the present invention will be explained below referring to FIG. 4. Moreover, in the explanation below, as for the same components explained in the first embodiment, the same reference numbers will be applied to, and explanation thereof will be omitted here.

The present embodiment differs from the above first embodiment in the point in that a sharp corrugated portion 24 is formed on the clamp face 12a of the high-frequency current forceps 23 of the present embodiment, while the clamp face 12a of the high-frequency current forceps of the first embodiment has a planar shape.

Other than the above, the high-frequency current forceps 23 has the same construction as that of the high-frequency current forceps 10 of the first embodiment.

Next, use of the high-frequency current forceps 23 will be explained below.

In the same manner as for the high-frequency current forceps 10 of the first embodiment, an endoscope (not shown in the figures) having this high-frequency current forceps 23 is inserted into a body cavity. Subsequently, the clamp pieces 12 and 13 clamp the treatment part 22 by controlling the sliding controller 19. At this time, even a slippery living organ can be reliably clamped without slipping because the shape of the corrugated portion 24 will increase the surface area of the clamp face 12a. Under this condition, high-frequency current is applied onto the electrode 18, and the treatment part 22 is then incised.

According to the high-frequency current forceps 23, the corrugated portion 24 prevents slipping when a tissue to be treated is clamped by the pair of clamp pieces 12 and 13. Therefore, excision can be performed safety and easily because it is possible to clamp a living organ in a stable manner, and to reliably supply current on the desired treatment part 22.

Figure 5:
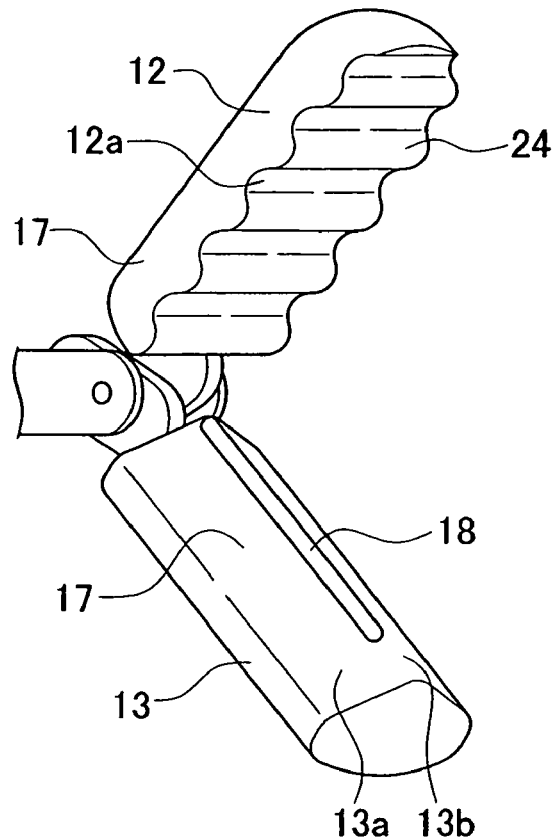
FIG. 5 is a perspective view of a variant example of the clamp pieces.

Moreover, the corrugated portion 24 can have a rounded shape as shown in FIG. 5. In the case in which such rounded shape is adopted, it becomes possible to reliably clamp the treatment part 22, and to decrease a possibility of peeling off of the insulation film 17 formed on the surface of the clamp piece 12.

Figure 6:
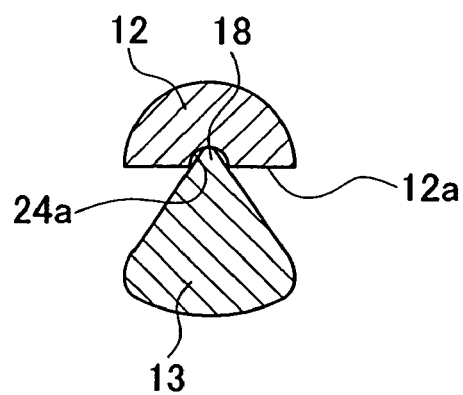
FIG. 6 is a cross-sectional view of another variant example of the clamp pieces.

In addition, as shown in FIG. 6, a concave portion 24a which joins with the electrode 18 may be further provided along the center portion, in the width direction of the clamp face 12a, of the corrugated portion 24 formed on the clamp face 12a. In the case in which such the concave portion 24a is provided, contacts between the electrode 18 and the treatment part 22 can be stronger.

Moreover, at the high-frequency forceps of the first and second embodiments, the clamp pieces 12 and 13 made of metal such as stainless steel covered with the insulation film 17 are adopted; however, it is not limited to this construction. For example, it is possible to adopt insulation material such as ceramics for the material of the clamp pieces 12 and 13, and to provide the separated electrode 18.

Third Embodiment

Next, a third embodiment of a high-frequency current treatment tool according to the present invention will be explained below referring to FIGS. 7 to 9.

Figure 7:
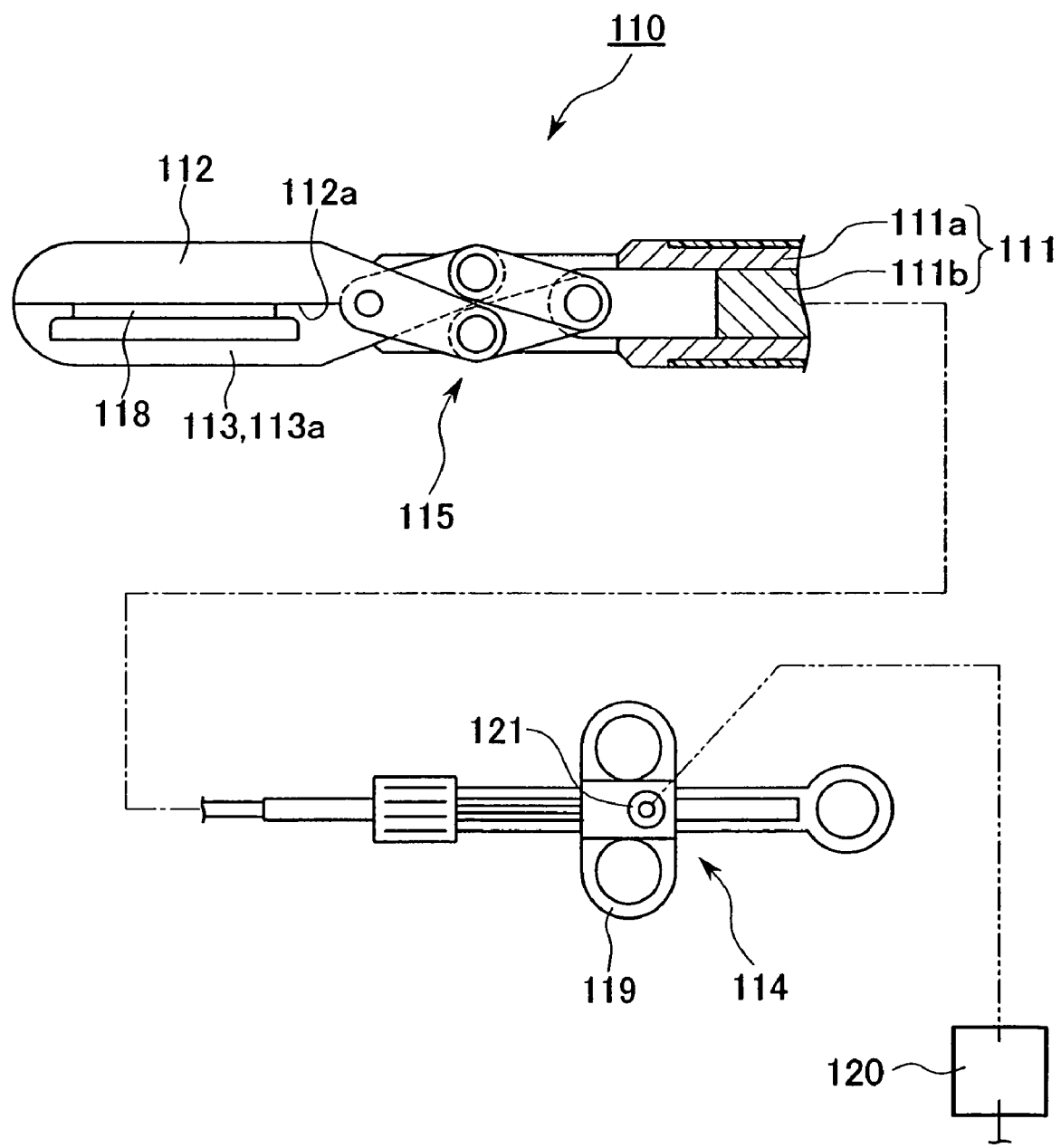
FIG. 7 is an explanatory view showing a high-frequency current forceps being a third embodiment of a high-frequency current treatment tool of the present invention.

As shown in FIG. 7, a high-frequency current forceps (a high-frequency current treatment tool) 110 according to the present embodiment has a flexible shaft part 111 to be inserted in a canal of an endoscope (not shown in the figures). A pair of clamp pieces 112 and 113 which faces with each other and extend along an axis of the shaft part 111 and clamps a living organ to be treated, is provided on a distal end of the shaft part 111. A control part 114 is provided on a proximal end of the shaft member 111.

The shaft part 111 includes a flexible tube 111a and a control wire 111b inserted in the flexible tube 111a. A distal end of the control wire 111b is connected to the pair of clamp pieces 112 and 113 via a link mechanism 115. An outer periphery of the flexible tube 111a is covered with an electrical insulation cover.

The clamp piece 112 is made of a metal such as a stainless steel, and a surface thereof is covered with an insulation film 117 having an electric non-conductance. The clamp piece 112 has a clamp face 112a facing the clamp piece 113.

Figure 8:
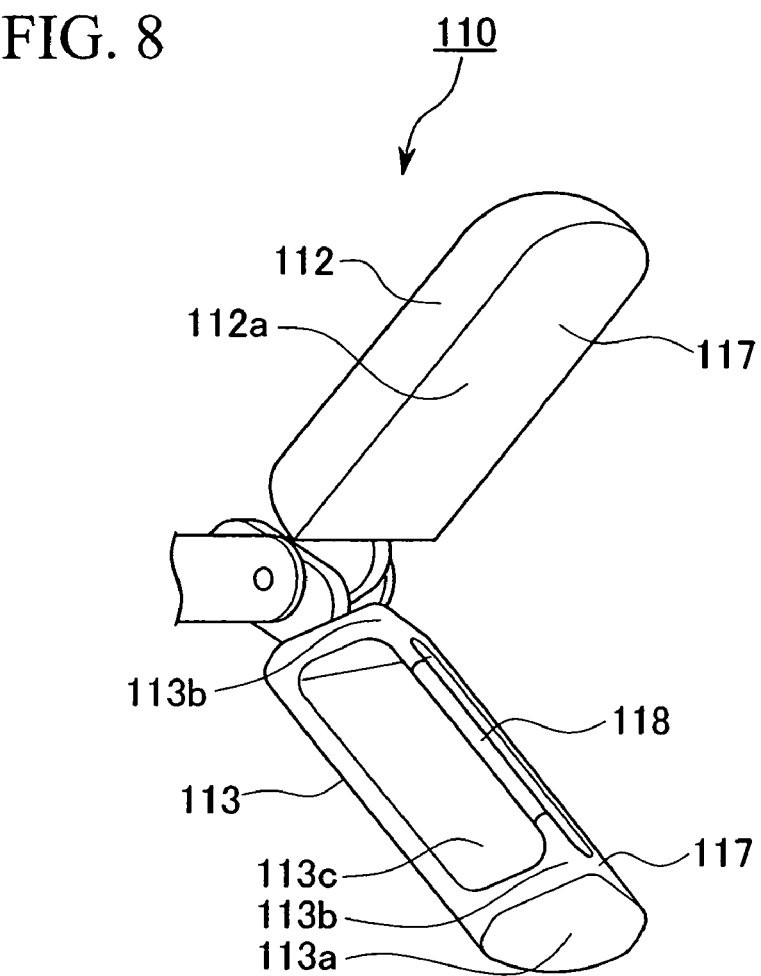
FIG. 8 is a perspective view of clamp pieces of the high-frequency current forceps.
Figure 9:
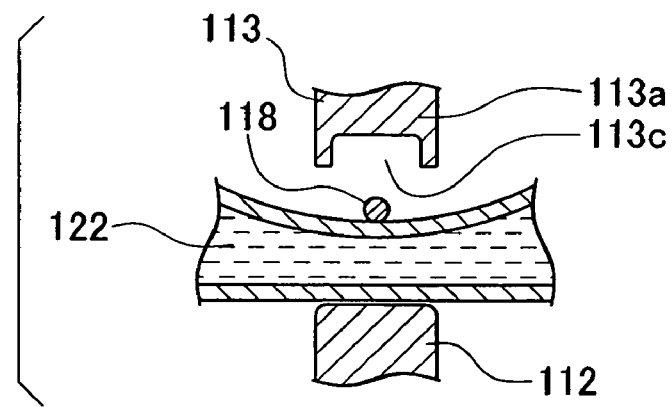
FIG. 9 is a cross-sectional view of a treatment part clamped by the high-frequency current forceps.

As shown in FIG. 8, the clamp piece 113 has a body 113a which is made of metal such as a stainless steel and is covered with the insulation film 117 having an electric non-conductance, and a wire 118 installed on the body 113a.

A ridgeline 113b is formed on the middle portion of the body 113a so as to extend along the length direction of the clamp piece 113. In addition, a large concave portion 113c is formed in the body 113a by removing a middle portion except for a distal end portion and a proximal end portion close to the shaft member 111.

Two ends of the wire 118 are supported by brazing them on the body 113a along the ridgeline 113b of the body 113a. By this, the wire 118 is held over the concave portion 113c so as to be arranged at the same position as of the ridgeline 113b.

One end of the wire 118 is electrically connected to the flexible tube 111a or the control wire 111b via a lead wire (not shown in the figures).

The control part 114 includes a sliding controller 119 to which one end of the control wire 111b is connected, and a connection plug 121 for electrically connecting between the wire 118 and one of the electrodes of a high-frequency current power supply 120. Another electrode (not shown in the figures) of the high-frequency current power supply 120 is connected to a skin of a human body so that a connection area therebetween is sufficiently larger than a connection area between the skin and the wire 118.

Next, use of the high-frequency current forceps 110 according to the present embodiment having the above-mentioned construction will be explained referring to FIG. 9.

Firstly, an endoscope not shown in the figures is inserted into a body cavity of a human body. Then, an injection needle (not shown in the figures) is inserted into the body cavity through the endoscope, and a treatment part 122 to be excised is enlarged by injecting physiological saline solution into a lower layer of a mucous membrane of the treatment part 122. Thereafter, the high-frequency current forceps 110 is inserted into the body cavity through the endoscope. At this time, the sliding controller 119 maintains its backward position, and the pair of clamp pieces 112 and 113 maintains their closed state.

Next, the high-frequency current forceps 110 is operated. By moving the sliding controller 119 forward, the link mechanism 115 is driven via the control wire 111b, and then the pair of clamp pieces 112 and 113 open. Then, after applying the clamp face 112a and the wire 118 on the enlarged treatment part 122, the sliding controller 119 is again pulled backward. Then, the link mechanism 115 is driven in opposite direction, and the pair of clamp pieces 112 and 113 close. The wire 118 makes a line-contact to the treatment part 122 and presses it, then clamps the treatment part 122 of the living organ together with the clamp face 112a. At this time, physiological saline solution or the like around the living organ diverges through the concave portion 113c without stagnation.

In this condition, when high-frequency current is supplied to the wire 118 by controlling the high-frequency current power supply 120, the high-frequency current is supplied through the human body to another electrode (not shown in the figures) pasted to the human body. At this time, current having very high electric current density flows near the wire 118 because a contact area between the wire 118 and the living organ is sufficiently small in relation to a size of the human body. As a result, the living organ contacting the wire 118 is excised.

In addition, because there is a concave portion 113c around the wire 118, physiological saline solution or the like will not remain around the wire 118; therefore, it is possible to prevent decreasing the electric current density due to divergence of current.

After the incision, the treatment part 122 is removed by removing the endoscope from the body cavity while maintaining the treatment part 122 clamped.

According to the high-frequency current forceps 110, because the wire 118 is used as an electrode, the surface area of the wire 118 can easily be made smaller by adjusting its external diameter; and therefore the electric current density can be increased. In addition, excision of the treatment part 122 can be done in a short time since electric current density can be increased.

Furthermore, because the two ends of the wire 118 are supported on the ridgeline 113b of the body 113a, only the treatment part 122 facing the clamp face 112a will contact the wire 118.

Figure 10:
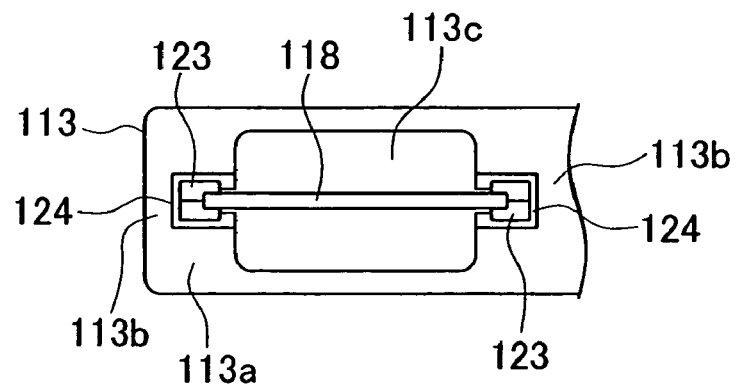
FIG. 10 is a plane view of a variant example of the clamp piece of the high-frequency current forceps.

Moreover, in the present embodiment, the wire 118 is fixed by brazing two ends thereof on the ridgeline 113b; however, the wire 118 may be fixed by an adhesive. Furthermore, as shown in FIG. 10, the wire 118 may be fixed by clamping the two ends with insulation members 123, and then inserting the two ends into supporting members 124 arranged on each end of the ridgeline 113b.

Fourth Embodiment

Figure 11:
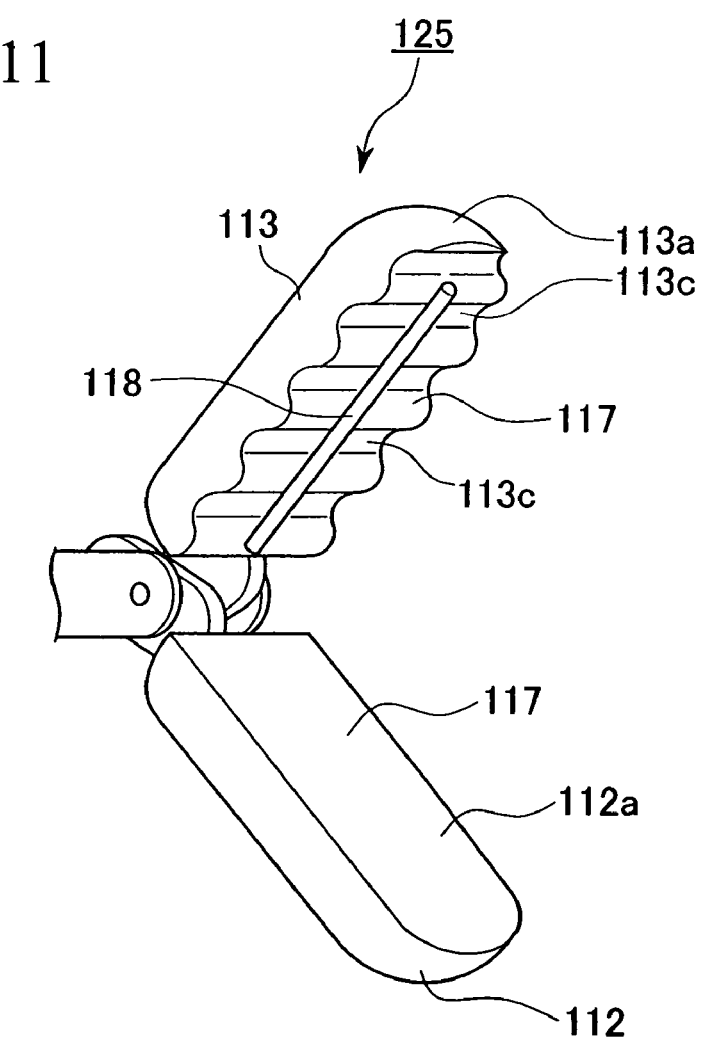
FIG. 11 is a perspective view of clamp pieces of a high-frequency current forceps being fourth embodiment of a high-frequency current treatment tool of the present invention.

Next, a fourth embodiment of a high-frequency current treatment tool of the present invention will be explained below referring to FIG. 11. In the explanation below, as for the same components as those explained in the third embodiment, the same reference numbers will be applied to and explanation thereof will be omitted here.

The present embodiment differs from the third embodiment in the point in that a high-frequency current forceps (a high-frequency current treatment tool) 125 of the present embodiment has a plurality of concave portions 113c instead of the single large concave portion 113c formed on the body 113a.

The concave portions 113c are formed so as to extend along a direction perpendicular to a length direction of the clamp piece 113 (i.e., a crossing direction in relation to a direction extending between a distal end portion and a proximal end portion of the clamp piece 113). Furthermore, the plurality of concave portions 113c is formed so as to be connected with each other along the length direction of the clamp piece 113.

The wire 118 is installed on the clamp piece 113 along the length direction of the clamp piece 113 so as to cross over the concave portions 113c.

Next, use of the high-frequency current forceps 125 according to the present embodiment will be explained.

As same as the high-frequency current forceps 110, an endoscope (not shown in the figures) having this high-frequency current forceps 125 is inserted into a body cavity. Subsequently, the clamp pieces 112 and 113 clamp the treatment part 122 by controlling the sliding controller 119. At this time, as same as in the third embodiment, the concave portions 113c will prevent physiological saline solution or the like remaining around the wire 118. Therefore, it becomes possible to perform a procedure, while reducing the likelihood of dispersion of current density due to electrical leakage via the physiological saline solution or the like to a living organ other than the treatment part 122, and the likelihood of damage on the electrical leakage portion. Furthermore, even a slippery living organ can be reliably clamped without slipping because the concave portions 113c can increase the surface area of the clamp face and thus can increase friction. Under this condition, high-frequency current is supplied to the wire 118, and then the treatment part 122 is excised.

According to the high-frequency current forceps 125, the concentration of current density can be maintained by the concave portions 113c, while reducing the likelihood of dispersion of the current density due to a physiological saline solution or the like. In addition, the concave portions 113c prevent slipping of a living organ clamped between the pair of clamp pieces 112 and 113; therefore, an operation becomes easier because it is possible to clamp the living organ in a stable manner, and to reliably supply current on the desired location of the treatment part 122.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, although the clamp pieces 112 and 113 of the third and fourth embodiments are made of a metal such as stainless steel covered with the insulation film 117, an insulation material such as a ceramics or the like may be adopted as the material instead of the metal.

Figure 12:
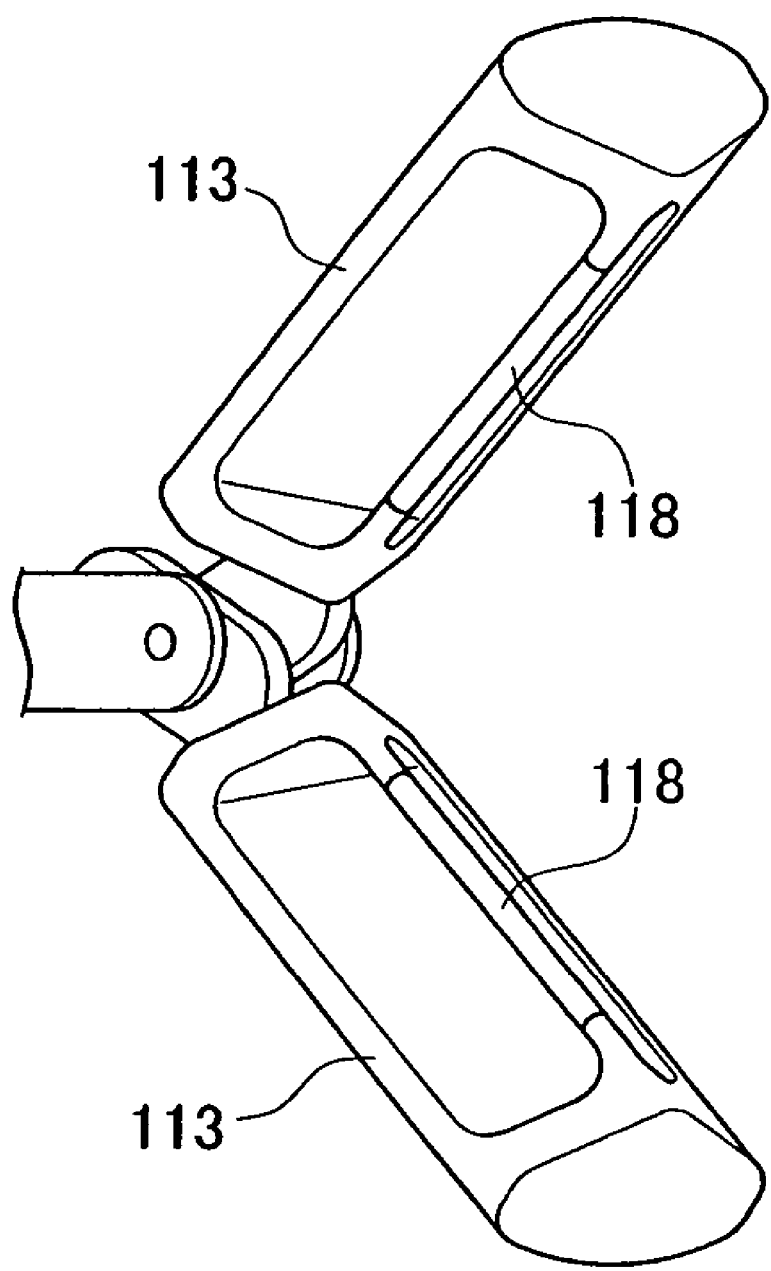
FIG. 12 is a perspective view of clamp pieces of a high-frequency current forceps being a fifth embodiment of a high-frequency current treatment tool of the present invention.

In addition, the high-frequency current forceps of the third and fourth embodiments adopt a configuration in that only one of the pair of clamp pieces has an electrode; however, it is not limited to this configuration. For example, as shown in FIG. 12, it is also possible to employ a high-frequency current forceps having a pair of clamp pieces 113 each of which has the wire 118 and which is openable and closable such that the wires 118 will approach to and depart from each other. In this case, the same operations and the same advantageous effects can be obtained as those of the third and fourth embodiments.

Next, a high-frequency current treatment tool according to the related technology of the present invention will be explained below. In the explanation below, for the same components explained in the third and fourth embodiments, the same symbols will be applied to and the explanation thereof will be omitted here.

Figure 13:
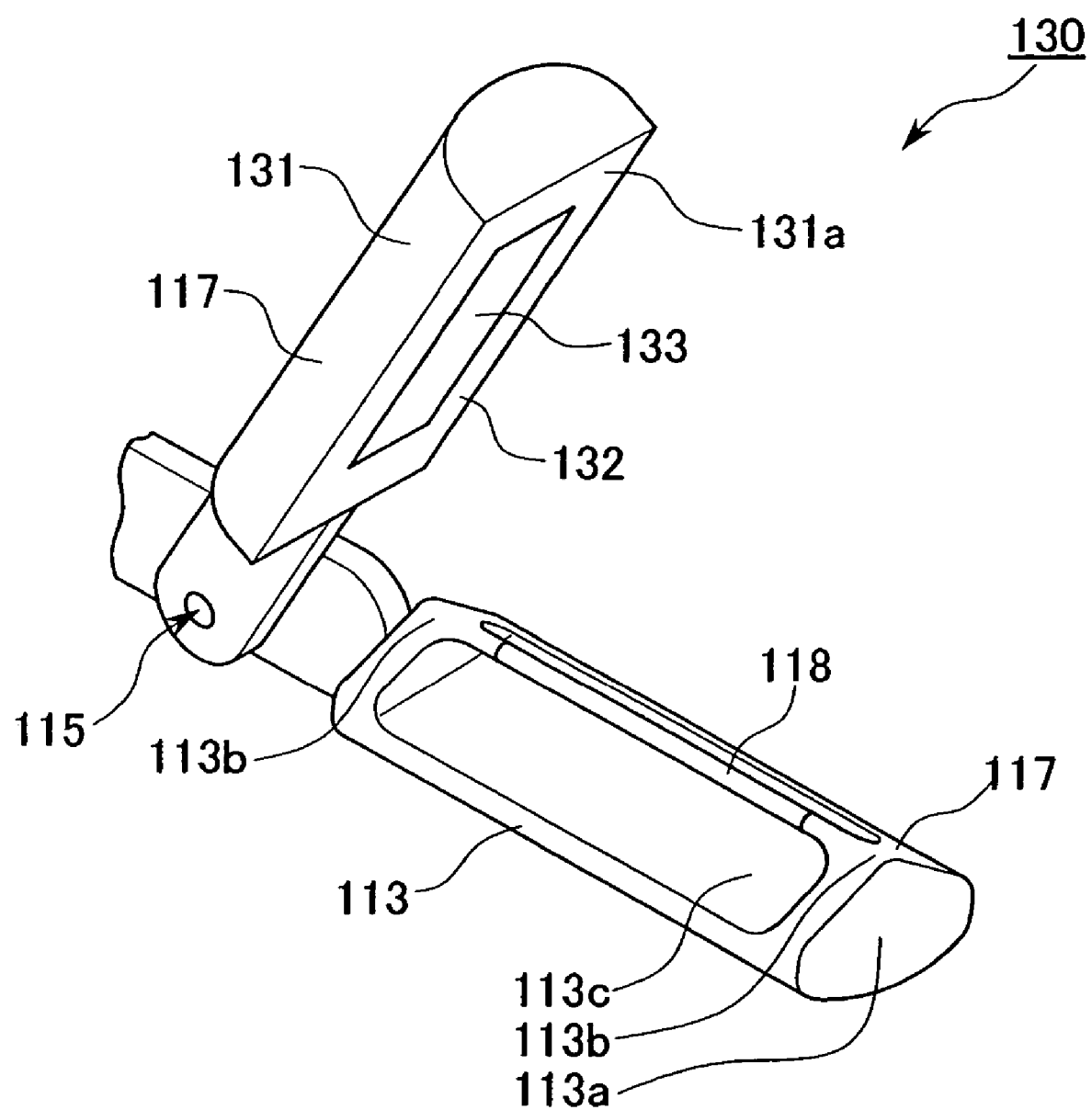
FIG. 13 is a perspective view of a high-frequency current forceps being a related technology of a high-frequency current treatment tool of the present invention.
Figure 14:
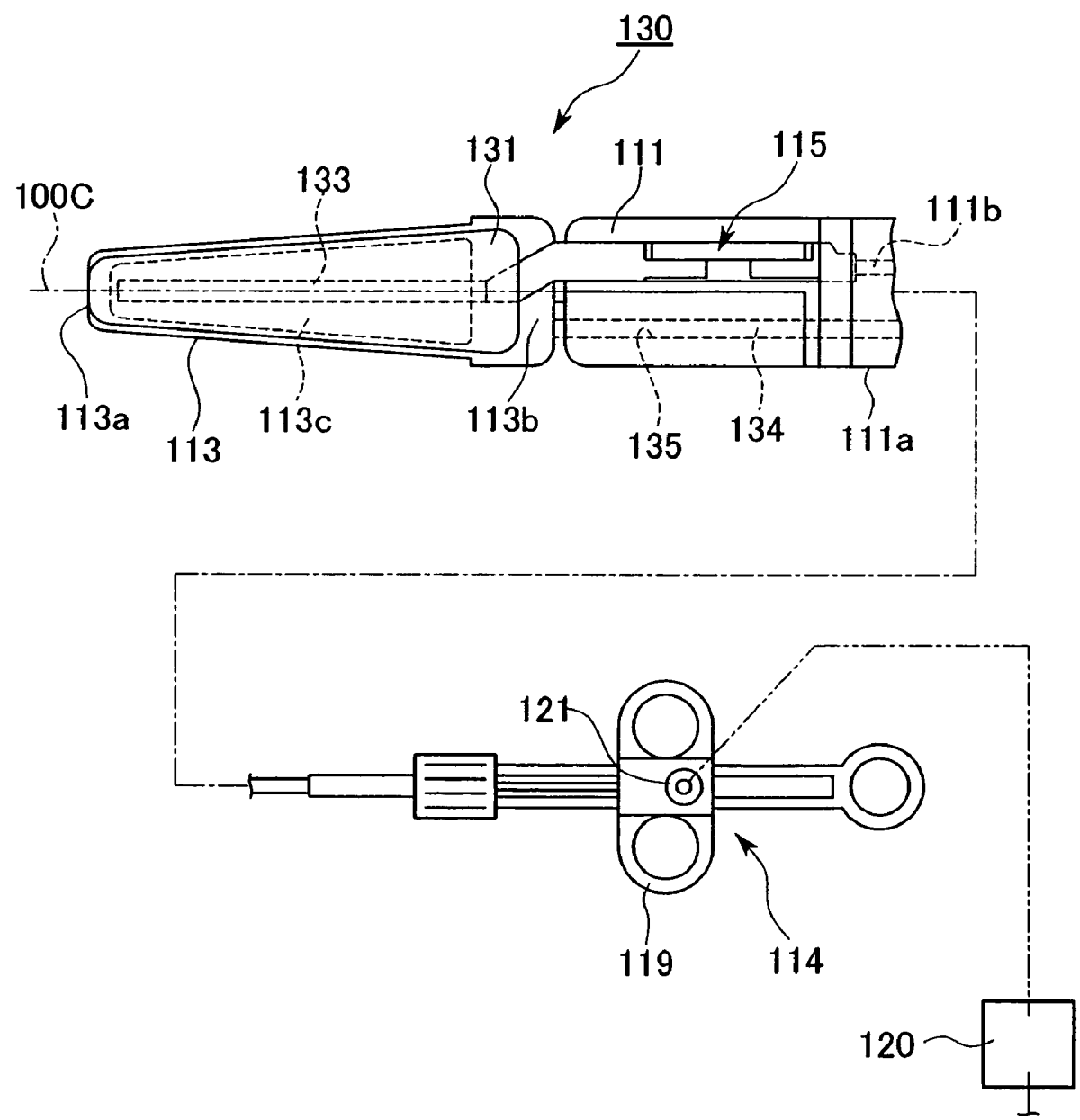
FIG. 14 is an explanatory view of a high-frequency current forceps being another related technology of a high-frequency current treatment tool of the present invention.

A high-frequency current forceps (a high-frequency current treatment tool) 130 according to the present related technology is, as shown in FIGS. 13 and 14, a bipolar type high-frequency current forceps which is used for incision or the like of a living organ by supplying high-frequency current between the clamp pieces 113 and 131.

In the conventional bipolar type high-frequency current forceps, high-frequency current is supplied to clamp pieces provided on its distal end portion by supplying the high-frequency current on a control wire which controls opening and closing actions of the clamp pieces 113 and 131.

A forceps is disclosed in FIG. 2 of the International Publication No. WO01/15614A1 which reduces the likelihood of current leakage by directly supplying high-frequency current on at least one of clamp pieces via an electric wire covered with an insulation material, in addition to supplying high-frequency current on a link mechanism.

The high-frequency current forceps 130 according to the present related technology has advantages in reducing the diameter and in insertion-and-retraction operability; therefore, it is also applicable to a flexible endoscope.

As shown in FIG. 14, the clamp piece 113 is fixed on a distal end of the shaft member 111 of the high-frequency current forceps 130. In addition, the clamp piece 131 is provided so as to face the clamp piece 113. Only the clamp piece 131 is connected to the link mechanism 115 so as to perform open-and-closing action.

Figure 15:
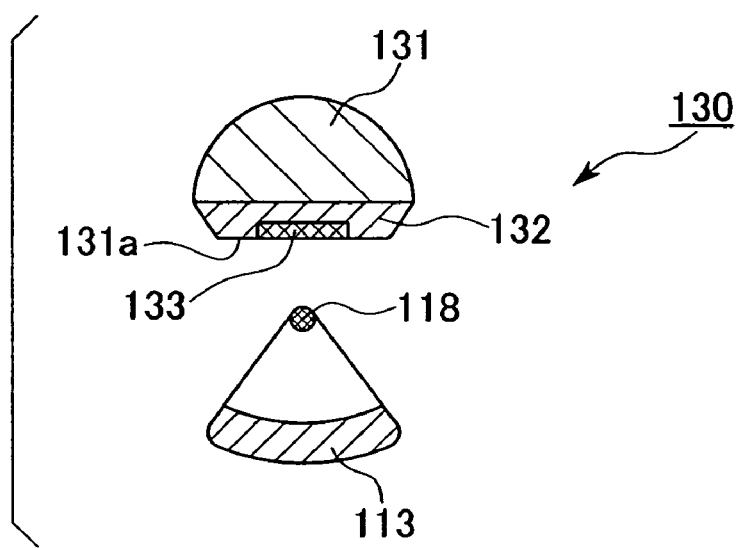
FIG. 15 is a cross-sectional view of clamp pieces of the high-frequency current forceps.

The clamp piece 131 is made of metal such as stainless steel, and has a clamp face 131a facing to the clamp piece 113. As shown in FIG. 15, the clamp face 131a is provided with: an electrode 132 formed by exposing a stainless portion; and a resin member 133 which is arranged at a location where contacts the wire 118 when closing the clamp pieces 113 and 131, and which extends toward a length direction of the clamp face 131a. The resin member 133 is made of a fluoro plastic or the like having electric non-conductance, and prevents a direct contact between the wire 118 and the electrode 132. A surface of the clamp piece 131 except for the clamp face 131a is covered with an insulation film 117 having electric non-conductance.

The link mechanism 115 of the present related technology has the same construction as that of the third embodiment. As shown in FIG. 14, the link mechanism 115 of the present related technology is arranged to one side in relation to a center axis 100C of the shaft member 111, and the link mechanism 115 is joined to the control wire 111b.

The insulated wire 134 is connected to a proximal end portion of the wire 118 provided to the clamp piece 113. The insulated wire 134 passes through a space 135 which is formed by shifting the link mechanism 115 and neighbors the link mechanism 115. Furthermore, the insulated wire 134 is placed inside the flexible tube 111a together with the control wire 111b, and then is connected to the high-frequency current power supply 120.

Next, use of the high-frequency current forceps 130 will be explained.

As same as the third and fourth embodiments, an endoscope having the high-frequency current forceps 130 is inserted into a body cavity. Subsequently, the clamp pieces 113 and 131 clamp the treatment part 122 by operating the sliding controller 119, then high-frequency current is supplied to the control wire 111b and the insulated wire 134 by operating the high-frequency current power supply 120. At this time, the high-frequency current passing through the control wire 111b, the link mechanism 115, and the wire 118, reaches to the electrode 132 via the treatment part 122. Then the high-frequency current returns from the electrode 132 to the high-frequency current power supply 120 through the insulated wire 134.

Accordingly, the high-frequency current having very high current density is applied between the wire 118 and the electrode 132 through the treatment part 122 clamped therebetween, and the treatment part 122 is incised.

According to the high-frequency current forceps 130, the link mechanism 115 is placed so as to be shifted in relation to the center axis 100C and so as to neighbor the insulated wire 134; therefore, it is possible to reduce the diameter of the shaft member 111 such that it can be used together with a flexible endoscope. Accordingly, the high-frequency current forceps can improve the insertion-and-retraction ability.

Figure 16:
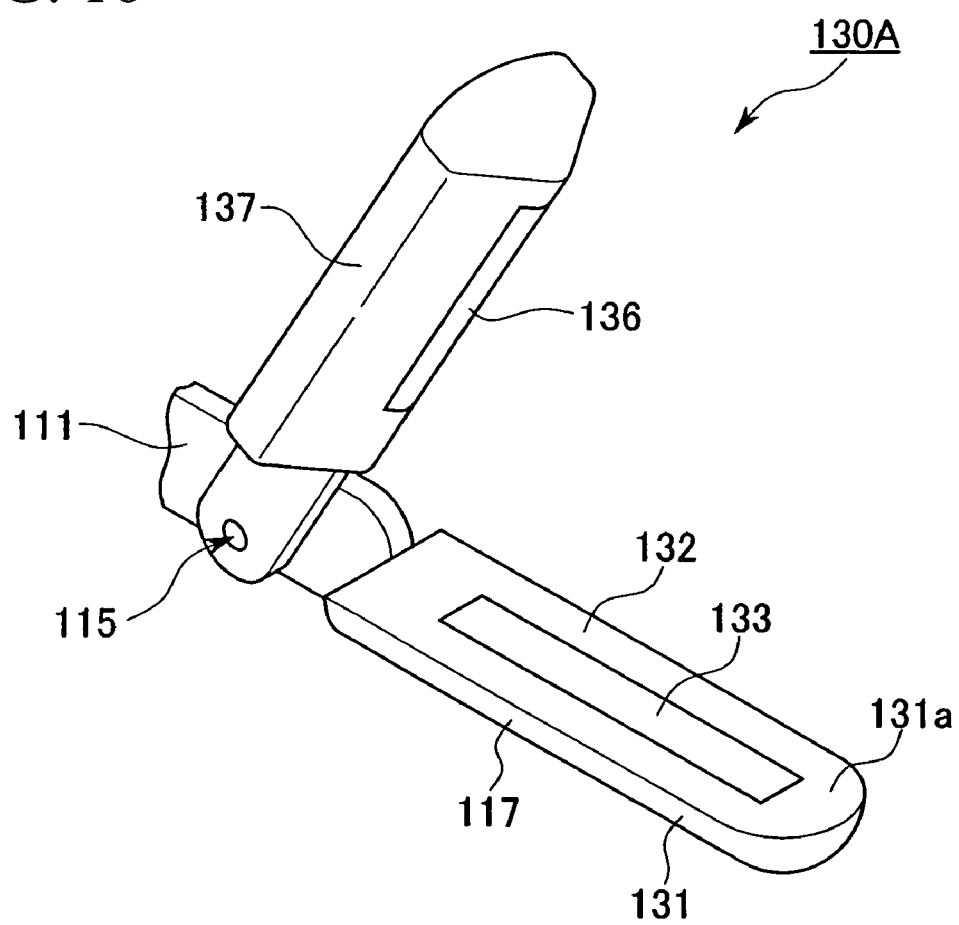
FIG. 16 is a perspective view of clamp pieces of another related technology of a high-frequency current treatment tool of the present invention.
Figure 17:
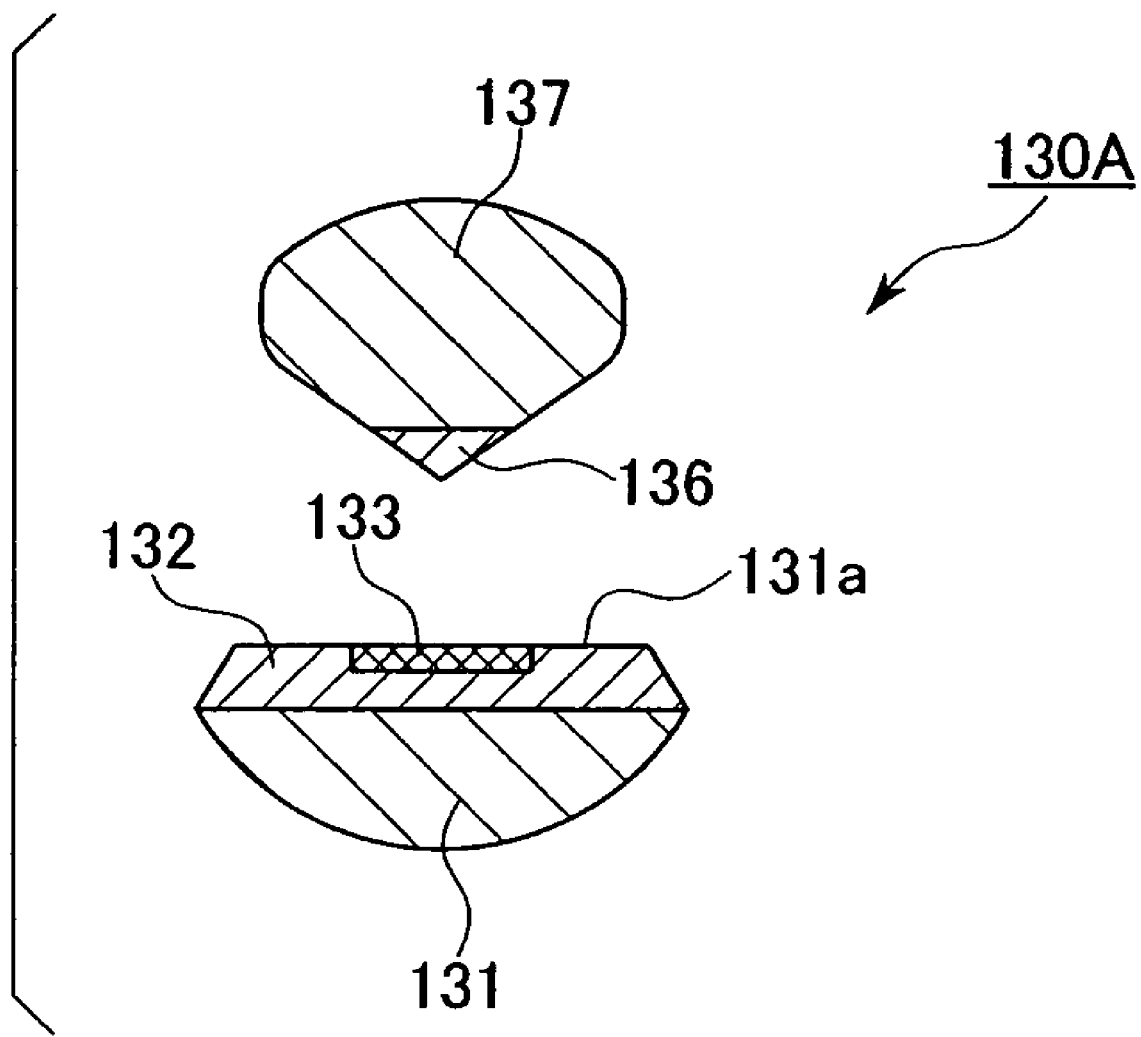
FIG. 17 is a cross-sectional view of the clamp pieces.

Moreover, as shown in FIGS. 16 and 17, it is also possible to adopt a high-frequency current forceps (a high-frequency current treatment tool) 130A having the clamp piece 131 fixed to a distal end of the shaft member 111, and a clamp piece 137 facing to the clamp piece 131 and connected to the link mechanism 115. This high-frequency current forceps 130A has a linear electrode 136 placed on a clamp face of the clamp piece 137 facing to the clamp piece 131 at the position where faces the resin member 133. The linear electrode 136 has a shape in which it follows along the length direction of the clamp piece 137 and sharply protrudes toward the clamp piece 131 in cross-section.

The high-frequency current forceps 130A also can have the same advantageous effects because it can produce the same high-frequency current between the electrode 132 and the linear electrode 136.

Figure 18:
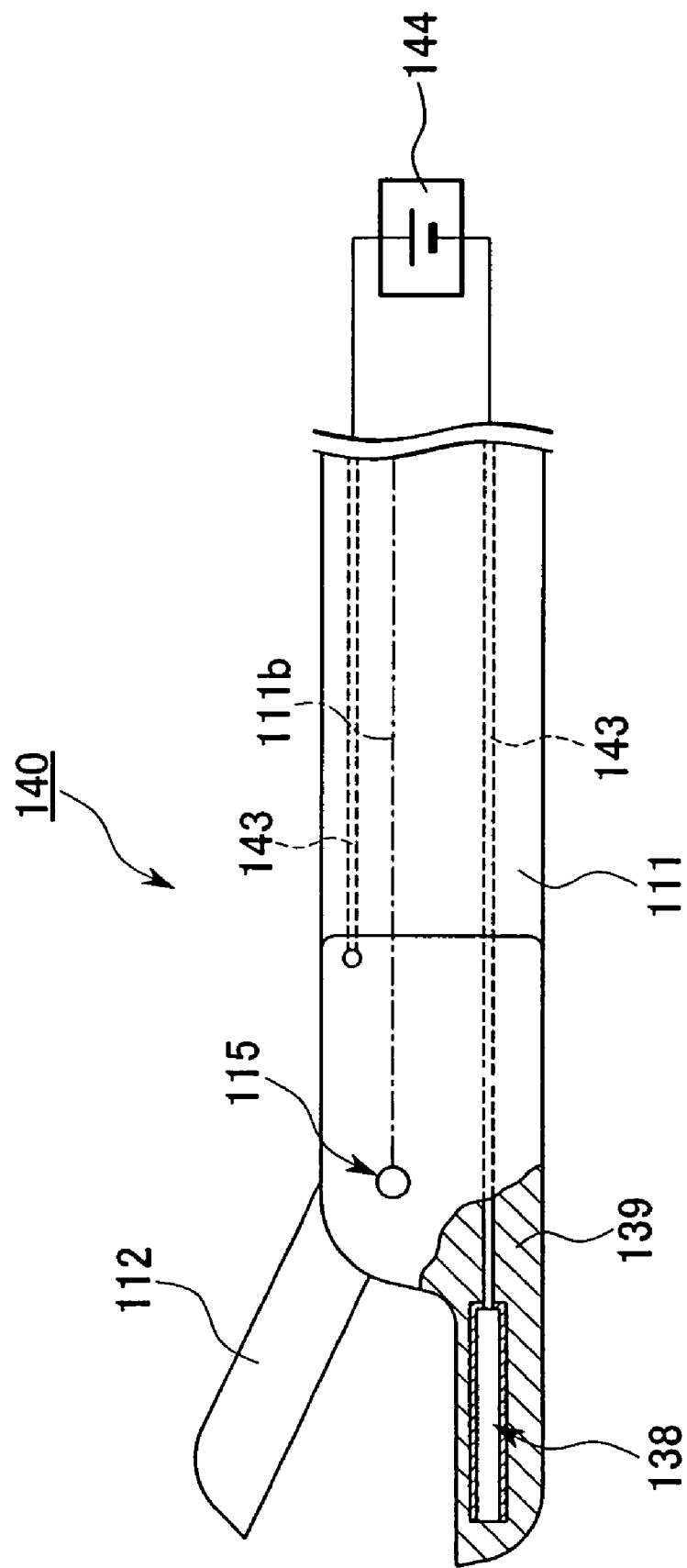
FIG. 18 is a side view of clamp pieces of a forceps being another related technology of the present invention.

Furthermore, as shown in FIGS. 18 and 19, it is possible to employ a forceps 140 having a clamp piece 139 in which a heat-emitting member 138 is placed instead of the electrode 132 and the linear electrode 136. This forceps 140 can incise the treatment part 122 using heat emitted from the heat-emitting member 138 by supplying direct-current on it instead of supplying the high-frequency current.

In this case, the clamp piece 112 of the third embodiment can be applied as a clamp piece facing to the clamp piece 139. The clamp piece 112 is connected to the control wire 111b via the link mechanism 115.

Figure 3:
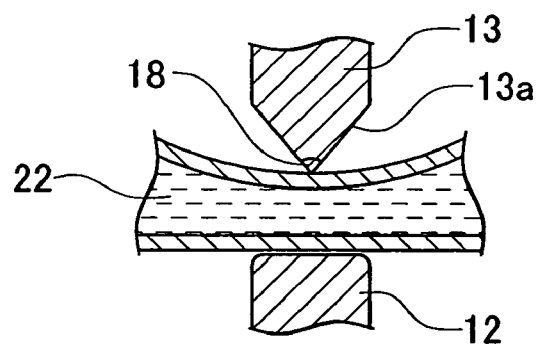
FIG. 3 is a cross-sectional view of a treatment part clamped by the high-frequency current forceps.

An example of a forceps which incises a living organ using emitted heat is disclosed in, for example, FIG. 3 of Japanese Unexamined Patent Application, First Publication No. 2001-340349.

The forceps 140 according to the present related-technology has advantages in reducing the diameter and in insertion-and-retraction operability; therefore, it is also applicable to a flexible endoscope.

In the forceps 140, a ridgeline portion 139b is formed extending along a length direction of the clamp piece 139 on a center portion of a clamp face 139a of the clamp piece 139 facing to the clamp piece 112. And the heat-emitting member 138 is installed inside the ridgeline portion 139b along the direction of the ridgeline portion 139b.

The heat-emitting member 138 includes a heater cover 141 and a heating element 142 installed inside the heater cover 141.

The heater cover 141 is made of an electrical insulation material such as ceramics, and is formed so as to extend along the ridgeline 139b. An opening portion 141A for exposing one end 142a of the heat element 142 is formed on a distal end face 141a of the heater cover 141. A penetration hole 141B is formed on a proximal end surface 141b to connect between another end 142b of the heat element 142 and an insulated line 143 for electrical power supply.

The insulated line 143 is placed inside the shaft member 111 together with the control wire 111b, and is connected to a direct-current power supply 144 together with the control wire 111b. Therefore, one end 142a of the heat element 142 is electrically connected to the clamp piece 139. And the another end 142b is electrically connected only to the insulated line 143 and is electrically insulated from the clamp piece 139.

Next, use of the forceps 140 will be explained.

As same as in the third embodiment, an endoscope (not shown in the figures) having the forceps 140 is inserted into a body cavity. Subsequently, the clamp pieces 112 and 139 clamp the treatment part 122 by operating the sliding controller 119, then direct current is supplied from the direct current power supply 144 to the control wire 111b and the insulated wire 134. The direct current reaches the clamp piece 139 via the control wire 111b through a distal end side of the shaft member 111, is then supplied to one end 142a of the heat element 142 through the opening portion 141A, and is then returned to the direct-current power supply 144 from another end 142b via the insulated line 143.

Meanwhile, the heat element 142 emits heat by the direct current flowing thereinside, and the treatment part 122 clamped between the clamp pieces 112 and 139 is then heated and incised.

According to the forceps 140, the shaft member 111 can be narrow so as to be useable together with a flexible endoscope because the heat element 142 is installed inside the clamp piece 139 together with the heater cover 141. Accordingly, operability for insertion-and-retraction of the forceps 140 in relation to an endoscope can be improved.

Features of high-frequency current treatment tools according to the above-explained embodiments of the present invention will be summarized in the following.

(1) A high-frequency current treatment tool of the present invention includes a pair of clamp pieces which clamps an object, and an electrode which is provided on one of the clamp pieces. Each of the clamp pieces has a clamp face which faces with each other. A first clamp face being one of the clamp faces has a chevron shape protruding toward a second clamp face being another of the clamp faces and having a ridge portion formed along a longitudinal direction of the first clamp face. The electrode is arranged along the ridge portion.

According to the high-frequency current treatment tool, when the pair of clamp pieces clamps the object therebetween, the first clamp face and the second clamp face will contact the object. Meanwhile, at the first clamp face, a portion of the object other than a treatment portion can be departed from the electrode along the chevron shape. Accordingly, treatment can be made while suppressing applying damages to the object except for a location where contacts the electrode.

(2) In the high-frequency current treatment tool according to the above (1), the electrode may be linear.

In this case, current density can be increased since the surface area of the electrode with respect to the first clamp face can be small. In addition, since a location of the object where the electrode contacts can be further limited, it becomes possible to more reliably suppress applying damages to the object except for a location contacting the electrode.

(3) In the high-frequency current treatment tool according to the above (2), a concave portion may be formed on the first clamp face at a middle position thereof in the longitudinal direction.

In this case, even if an unfavorable object (e.g., water such as physiology salt solution) exists around the electrode while clamping the object, the unfavorable object can be removed from the around of the electrode by introducing it into the concave portion. Accordingly, since reduction in the current density due to the unfavorable object for procedures can be suppressed, it is possible to maintain the concentration of the current density while performing procedures.

(4) In the high-frequency current treatment tool according to the above (3), the concave portion may be formed at a position between a distal end portion and a proximal end portion of the first clamp face along the ridge portion.

In this case, the electrode can be installed after processing the first clamp face; therefore, the first clamp face can be processed easily. Accordingly, the flexibility in processing can be increased.

(5) In the high-frequency current treatment tool according to the above (4), the electrode may be installed at a position between a first ridge portion on the distal end portion and second ridge portion on the proximal end portion.

In this case, the same operations and advantageous effects can be obtained as those of the high-frequency current treatment tool according to the above (4).

(6) In the high-frequency current treatment tool according to the above (2), the electrode may be a wire.

In this case, surface area of the electrode can be reduced by adopting the wire having a smaller diameter; therefore, the current density can be increased easily. Accordingly, it is possible to easily and reliably perform procedures only for the treatment part in the object.

(7) In the high-frequency current treatment tool according to the above (1), a corrugated portion may be formed on the second clamp face.

In this case, while sandwiching the object by the pair of clamp pieces, even a slippery object can be firmly clamped and be treated without slipping because the corrugated portion will increase the friction of the second clamp face.

(8) In the high-frequency current treatment tool according to the above (1), the electrode may be provided inside a distal end of the first clamp face.

In this case, since the electrode will not be out of the first clamp face, it becomes possible to perform procedures while more reducing influences on the around of the treatment part where contacts the first clamp face.

(9) In the high-frequency current treatment tool according to the above (1), a plurality of concave portions each of which crosses a longitudinal direction of the second clamp face may be formed on the second clamp face.

In this case, even if an unfavorable object (e.g., water such as physiology salt solution) exists on the second clamp face while clamping the object, the unfavorable object can be removed from the second clamp face by introducing it into the concave portions. Accordingly, since the reduction in the current density due to the unfavorable object for procedures can be suppressed, it is possible to maintain the concentration of the current density while performing procedures. Furthermore, since the concave portions will increase the surface area and the friction of the second clamp face, even a slippery object can be firmly clamped. Accordingly, procedures becomes easier since the object can be held stably.

(10) Another high-frequency current treatment tool of the present invention includes a pair of clamp pieces which clamps an object, and a pair of electrodes each of which is provided on the clamp pieces. Each of the clamp pieces has a clamp face which faces with each other. Each of the clamp faces has a chevron shape protruding toward another clamp face and having a ridge portion formed along a longitudinal direction of the clamp face. Each of the electrodes is arranged along the ridge portions.

According to the high-frequency current treatment tool, when the pair of clamp pieces clamps the object therebetween, each of the clamp faces will contact the object. Meanwhile, at the both of the clamp faces, a portion of the object other than a treatment portion can be departed from the electrode along the chevron shape. Accordingly, treatment can be made while suppressing applying damages to the object other than a location where contacts the electrode.

(11) In the high-frequency current treatment tool according to the above (10), the electrodes may be linear.

In this case, current density can be increased since the surface area of the electrode with respect to the clamp face can be small. In addition, since a location of the object where the electrode contacts can be further limited, it becomes possible to more reliably suppress applying damages to the object other than a location where contacts the electrode.

(12) In the high-frequency current treatment tool according to the above (11), each of the electrodes may be a wire.

In this case, surface area of the electrode can be reduced by adopting the wire having a smaller diameter; therefore, the current density can be increased easily. Accordingly, it is possible to easily and reliably perform procedures only for the treatment part in the object.

(13) In the high-frequency current treatment tool according to the above (11), a concave portion may be formed on each of the clamp faces at middle positions thereof in the longitudinal direction.

In this case, even if an unfavorable object (e.g., water such as physiology salt solution) exists around the electrode while clamping the object, the unfavorable object can be removed from the around of the electrode by introducing it into the concave portions. Accordingly, since the reduction in the current density due to the unfavorable object for procedures can be suppressed, it is possible to maintain the concentration of the current density when performing procedures.

(14) In the high-frequency current treatment tool according to the above (13), each of the concave portions may be formed at a position between a distal end portion and a proximal end portion of the clamp faces along the ridge portion.

In this case, the electrodes can be installed after processing the clamp faces; therefore, the clamp faces can be processed easily. Accordingly, the flexibility in processing can be increased.

(15) In the high-frequency current treatment tool according to the above (14), each of the electrodes may be installed at a position between a first ridge portion on the distal end portion and a second ridge portion on the proximal end portion.

In this case, the same operations and advantageous effects can be obtained as those of the high-frequency current treatment tool according to the above (13).

(16) In the high-frequency current treatment tool according to the above (10), each of the electrodes may be provided inside a distal end of the clamp face.

In this case, since the electrodes will not be out of the clamp faces, it becomes possible to perform procedures while more reducing influences on the around of the treatment part where contacts the clamp faces.

(17) Another high-frequency current forceps of the present invention includes: a pair of electrically insulated clamp faces facing with each other; and a linear electrode provided on one of the clamp faces.

According to the high-frequency current forceps, because the linear electrode is provided on only one of the clamp faces, the surface area of the electrode in the clamp face can easily be made smaller compare to a conventional one; therefore, current density can be increased. Furthermore, because a treatment part which contacts the electrode can be limited to one which contacts an internal area of the clamp face, safe operation can be performed by decreasing the likelihood of applying electrical damage to a living organ other than a location where contacts the electrode.

Therefore, according to the high-frequency current forceps of the present invention, because the electrode is provided on one of the clamp faces, current density can be more concentrated by making the surface area of the electrode smaller, and thus operation performance can be improved by easily and firmly operating only a tissue which should be treated.

(18) In the high-frequency current treatment tool according to the above (17), a corrugated portion may be formed on at least one of the clamp faces.

In this case, the corrugated portion can prevent slipping when a tissue is clamped between the pair of clamp faces by increasing friction force. Therefore, the treatment can be done easily by firmly clamping the treatment part.

(19) In the high-frequency current treatment tool according to the above (17), the electrode may be provided inside an area formed by a tip edge of the clamp face.

In this case, because the electrode will not be exposed on a surface of the clamp piece other than the clamp face, the high-frequency current forceps can perform treatment while decreasing an affect on a living organ other than the treatment part.

(20) In the high-frequency current treatment tool according to the above (17), the electrode may be a wire of which the two ends are supported on the clamp face.

In this case, current density can be increased because the electrode is a wire and the surface area of the electrode can easily be made smaller by adopting a smaller wire diameter. In addition, the clamp face can be processed more easily because the electrode can be installed later on the insulated clamp face. Therefore, the high-frequency current forceps can be manufactured more easily.

(21) Another high-frequency current treatment tool of the present invention includes a pair of clamp pieces, wherein at least one of the clamp pieces includes: an electrically insulated body on which a concave portion is formed on a clamp face of the body; and a linear electrode having two ends supported above the concave portion.

According to the high-frequency current treatment tool of the present invention, current density can be increased because a surface area of the linear electrode contacting a living organ can be smaller in relation to a conventional high-frequency current treatment tool, by adopting the linear electrode. In addition, because the two ends of this linear electrode are supported on the body, only the treatment part facing the clamp face can contact the linear electrode. Furthermore, because the linear electrode is supported above the concave portion formed on the body, water leaking out from the living organ when clamping the living organ can be removed from the linear electrode through the concave portion. Therefore, decreasing of current density due to water can be prevented, thus concentration of the current density during an operation can be maintained.

Therefore, according to the high-frequency current treatment tool of the present invention, because the linear electrode of which two ends are supported on the body of the clamp piece is provided, current density can be concentrated by adopting a linear electrode having a smaller surface area, and thus operability can be improved by easily and firmly operating only a treatment part which should be operated.

(22) In the high-frequency current treatment tool according to the above (21), the concave portion may be formed between a distal end portion and a proximal end portion of the body; and the two ends of the linear electrode may be supported on the distal end portion and the proximal end portion.

(23) In the high-frequency current treatment tool according to the above (22), a ridgeline extending between the distal end portion and the proximal end portion except for the concave portion may be formed on the clamp face, and the two ends of the linear electrode may be supported on the ridgeline.

(24) In the high-frequency current treatment tool according to the above (21), a wire may be used as the linear electrode.

In this case, current density can be increased because surface area of the electrode can easily be smaller by decreasing the diameter of the wire. In addition, the clamp face can be processed more easily because the electrode can be installed later on the insulated clamp face.

(25) Another forceps for an endoscope of the present invention includes a pair of clamp pieces, wherein at least one of the clamp pieces include: an electrically insulated body on which a plurality of concave portions are formed on a clamp face of the body along a crossing direction in relation to a direction extending between a distal end portion and a proximal end portion of the clamp face; and a linear electrode which is supported above the concave portions.

(26) In the high-frequency current treatment tool according to the above (25), a wire may be used as the linear electrode.

What is claimed is:

1. A high-frequency current treatment tool comprising:
a pair of clamp pieces which clamps an object, and
an electrode, wherein:
each of the clamp pieces has a clamp face which faces with each other;
a first clamp face being one of the clamp faces, the first clamp face consisting of:
a pair of inclined surfaces; and
a ridge portion provided at an intersection of the pair of inclined surfaces, wherein:
the ridge portion is formed along a longitudinal direction of the first clamp face, and
the pair of inclined surfaces and the ridge portion define a chevron shape protruding toward a second clamp face being another of the clamp faces;
the electrode is linear and is provided only on the first clamp face so as to be arranged along the ridge portion;
a corrugated portion is provided on the second clamp face;
a surface of each of the pair of clamp pieces, except for the place where the electrode is provided, is insulated, and
a distal end of the electrode is located on a more proximal side than a distal end of the first clamp face.

2. The high-frequency current treatment tool according to claim 1, wherein a concave portion is formed on the first clamp face at a middle position thereof in the longitudinal direction.

3. The high-frequency current treatment tool according to claim 2, wherein the concave portion is formed at a position between a distal end portion and a proximal end portion of the first clamp face along the ridge portion.

4. The high-frequency current treatment tool according to claim 3, wherein the electrode is installed at a position between a first ridge portion on the distal end portion and a second ridge portion on the proximal end portion.

5. The high-frequency current treatment tool according to claim 1, wherein the electrode is a wire.

6. The high-frequency current treatment tool according to claim 1, wherein a plurality of concave portions each of which crosses a longitudinal direction of the second clamp face are formed on the second clamp face.

* * * * *